United States Patent
Gasco

(10) Patent No.: US 6,685,960 B1
(45) Date of Patent: Feb. 3, 2004

(54) SOLID LIPIDIC NANOSPHERES SUITABLE TO A FAST INTERNALIZATION INTO CELLS

(76) Inventor: Maria Rosa Gasco, Lungo Po Antonelli 207, 10153 Torino (IT)

( * ) Notice: Subject to any disclaimer, the term of this patent is extended or adjusted under 35 U.S.C. 154(b) by 0 days.

(21) Appl. No.: 09/856,266
(22) PCT Filed: Nov. 24, 1999
(86) PCT No.: PCT/EP99/09072
  § 371 (c)(1),
  (2), (4) Date: May 17, 2001
(87) PCT Pub. No.: WO00/30620
  PCT Pub. Date: Jun. 2, 2000

(30) Foreign Application Priority Data

Nov. 25, 1998 (IT) .......................... MI98A2557

(51) Int. Cl.⁷ ............................... A61K 9/127
(52) U.S. Cl. .................... 424/450; 264/4.4; 424/489
(58) Field of Search ................... 264/4.4, 115, 118, 264/122; 424/489, 490, 491, 400; 427/2.14

(56) References Cited

U.S. PATENT DOCUMENTS 4,544,545 A * 10/1985 Ryan et al. ............... 424/1.1
5,250,236 A * 10/1993 Gasco ...................... 264/4.4

FOREIGN PATENT DOCUMENTS

| EP | 526666 | 2/1993 | ............ | A61K/9/51 |
| WO | WO 94/20072 | * 9/1994 | | |
| WO | WO9420072 | 9/1994 | ............ | A61K/9/10 |
| WO | WO9856362 | 12/1998 | ............ | A61K/9/51 |

OTHER PUBLICATIONS

Langdon et al., "Effect of Sodium Butyrate and Other Differentiation Inducers on Poorly Differentiated Human Ovarian Adenocarcinoma Cell Lines", *Cancer Research*, 48, pp. 6161–6165 (1988).

Yamamoto et al., "Suppression of Growth of Hepatocellular Carcinoma by Sodium Butyrate in Vitro and In Vivo", *Int. J. Cancer*, 76, pp. 897–902 (1998).

Velazquez et al., "In Vivo Crypt Surface Hyperproliferation is Decreased by Butyrate and Increased by Deoxycholate in Normal Rat Colon: Associated In Vivo Effects on c–Fos and c–Jun Expression" *Journal of Parenteral and Enteral Nutrition*, vol. 20, No. 4, (1996).

Mandal and Kumar, "Bcl–2 Expression Regulates Sodium Butyrate–induced Apoptosis in Human MCF–7 Breast Cancer Cells", *Cell Growth and Differentiation*, vol. 7, 311–318, Mar. 1996.

Perrine et al., "A Short–Term Trial of Butyrate to Stimulate Fetal–Globin–Gene Expression in the β–Globin Disorders", *The New England Journal of Medicine*, vol. 328, No. 2, pp. 81–85 (1993).

Collins et al., "Oral Sodium Phenylbutyrate Therapy in Homozygous β Thalassemia: A Clinical Trial", *Blood*, vol. 85, No. 1, pp. 43–49, (1995).

Cavalli et al., "Behavior of Timolol Incorporated in Lipospheres in the Presence of a Series of Phosphate Esters", *S.T.P. Pharma Sciences* 2 (6) 514–518 (1992).

Cavalli et al., "Sterilization and Freeze–Drying of Drug–Free and Drug–Loaded Solid Lipid Nanoparticles", *International Journal of Pharmaceutics*, 148, pp. 47–54 (1997).

Carney et al., "Establishment and Identification of Small Cell Lung Cancer Cell Lines Having Lung Cancer Cell Lines Having Classic and Variant Features", *Cancer Research*, vol. 45, Jun. 1985.

* cited by examiner

Primary Examiner—Thurman K. Page
Assistant Examiner—S. Tran
(74) Attorney, Agent, or Firm—Abelman, Frayne & Schwab

(57) ABSTRACT

The present invention relates to pharmaceutical compositions in form of solid lipidic nanospheres able to rapidly penetrate into the cells, comprising as an active substance a lipidic substance consisting of an ester of α-tocopherol or δ-tocopherol or of cholesterol or of glycerol with a carboxylic acid selected from acetic acid, propionic acid, butyric acid and succinic acid, useful in the treatment of tumoral pathologies and of Mediterranean anaemia.

9 Claims, No Drawings

SOLID LIPIDIC NANOSPHERES SUITABLE TO A FAST INTERNALIZATION INTO CELLS

FIELD OF THE INVENTION

The present invention relates to pharmaceutical compositions in form of solid lipidic nanospheres able to fast penetrate into the cells, the process for their preparation and their use in the treatment of tumoral pathologies and of Mediterranean anaemia.

PRIOR ART

It is known from literature that the carboxylic acids having a low number of carbon atoms, such as acetic acid, propionic acid, butyric acid and succinic acid, and their derivatives, may inhibit the proliferation of the tumoral cells, in particular in the case of colon cancers (H. P. Scheppach, F. Ritcher, Eur. J. Cancer Prevention, 4, 373–378, 1995, and 31, 1077–1080, 1995).

There are in particular experimental proofs showing the antiproliferative activity of the butyric acid salts, for example of the sodium salt, towards a great variety of neoplastic cells (S. P. Landon et al., Cancer res., 48, 6161–6165, 1988; D. Coradini et al., Cell Prolif., 30, 149–159, 1997; H. Yamamoto et al., Int. J. Cancer, 76, 897–902, 1998). Recent studies showed that sodium butyrate is able to modulate the expression of the oncogenes and of the genes regulating the apoptosis in cells from different histotypes (O. C. Velasquez et al., J. Parenteral Enteral Nutr., 20, 243–250, 1996; M. Mandal, R. Kumar, Cell Growth Diff., 7, 311–318, 1996).

It is moreover known that the carboxylic acids themselves andlor certain derivatives thereof may help in a significant way, in the case of the Mediterranean anaemia, the transformation of $\beta$-globin to $\gamma$-globin, or fetal globin, resulting in an improvement of the disease (S. P. Perine et al., New England J. Medicine, 328, 81–86, 1993, A. F. Collins et al., Blood, 85, 43–49, 1995).

At present, the use of such compounds is however strongly limited by the difficulty in reaching effective plasmatic concentrations, owing to the short half-life time, which makes the metabolism and the excretion of said substances too fast. In order to obtain satisfactory results therefore one ought to administrate high amounts of acid, with the drawback of causing harmful side effects.

Therefore one feels the need to have an adequate system of release for these substances, which allows to decrease their doses, thus minimising the side effects.

The document WO 94/20072 (Westesen K. at al.) describes particles of bioactive agents wherein the matrix is constituted by the bioactive agent itself. Substances particularly suitable for the formulation as said particles are drugs and other bioactive materials which are poorly water soluble. A long list of said substances, from anesthetics to virustatics, comprising tocopherol acetate and tocopherol succinate is reported.

No information about the internalization of said particles into cells is given.

SUMMARY

Now the Applicant found new pharmaceutical compositions allowing to overcome the drawbacks of the prior art, showing a surprisingly high biological activity.

Said pharmaceutical compositions are prepared in form of solid lipidic nanospheres characterised in that they comprise as an active substance a lipidic substance consisting of cholesteryl butyrate and if necessary one or more further pharmacologically active substances.

A further object of the present invention is the process for the preparation of said lipidic nanospheres, comprising the following steps:

a) heating of a mixture comprising a lipidic substance and one or more surfactants at a temperature such as to take the mixture to melting;

b) heating of a mixture consisting of water and one or more co-surfactants at a temperature at least equal to the step a) one;

c) hot mixing under mild stirring of the mixture of the step b) with the mixture of the step a), with the achievement of a microemulsion;

d) dispersion of the microemulsion obtained in the step c) in pre-cooled water;

e) washing of the dispersion of the step d) with distilled water by diafiltration;

f) freeze-drying of the product obtained in the step e) or its hot sterilisation, characterised in that said lipidic substance consists of cholesteryl butyrate.

The pharmaceutical compositions in form of solid lipidic nanospheres object of the present invention are useful in the treatment of all the pathological conditions for which the administration of the above mentioned carboxylic acids is effective, and they are particularly suitable for the treatment of tumoral pathologies and of the Mediterranean anaemia.

The characteristics and the advantages of the solid lipidic nanospheres as a release system for the carboxylic acids according to the present invention and of the related preparation process will be pointed out in detail in the following description.

DETAILED DESCRIPTION OF THE INVENTION

The present invention relates to pharmaceutical compositions in form of solid lipidic nanospheres obtained from microemulsions of a lipidic substance, stabilised by at least a surfactant and by one or more cosurfactants.

With the term lipidic nanospheres in the present invention we mean particles having an average diameter lower than 300 nm.

For the preparation of said microemulsions a lipidic substance in a mixture with one or more surfactants, and if necessary one or more further pharmacologically active substances, is heated to melting; separately a mixture consisting of water and one or more cosurfactants is heated to a temperature at least equal to that one at which the mixture containing the lipidic substance melts. The aqueous mixture is then hot added under mild stirring to the mixture containing the lipidic substance, obtaining a microemulsion.

The so obtained microemulsion is poured into precooled water at a temperature ranging from 2 to 10° C. under mild stirring, using a water amount ranging from 10:1 to 80:1 parts by volume with respect to the volume of the microemulsion. The so obtained dispersion is then washed many times with distilled water by diafiltration in order to remove the components soluble in water, using a TCF2 equipment (Amicon-Grace-Danvers, USA) equipped with a YM 100 Diaflo membrane with a 100,000 Dalton cut-off, as disclosed in R. Cavalli et al., S. T. P. Pharma Sciences, 2(6), 514–518, 1992.

Such dispersion is finally hot sterilised in autoclave at 121° C. for 15 minutes at 2 atm, or freeze-dried.

The so obtained lipidic nanospheres have an average diameter ranging from 40 to 300 nm, and preferably from 100 to 200 nm, and a polydispersion index ranging from 0.10 to 0.50.

The characterisation of the microemulsions has been carried out by photocorrelation spectroscopy with a N 4 Coulter instrument, as disclosed in R. Cavalli et al., Int. J. Pharm., 148, 47–54, 1997.

Said lipidic substance constitutes the essential active substance of the lipidic nanospheres, which however may include, in particular embodiment forms of the present invention, one or more other pharmacologically active substances.

Such further active substances are typically selected from the group consisting of doxorubicin, idarubicin and taxol.

According to a preferred embodiment form of the present invention said lipidic substance is cholesteryl butyrate.

As surfactants phosphatidylcholine taken from soy or egg yolk, phospholipids and their mixtures are typically used.

According to a preferred embodiment form of the present invention the used surfactant is a commercial product known with the name Epikuron 200® (Lukas Meyer, Hamburg, Germany), consisting of phosphatidylcholine for 95%.

The cosurfactants are selected from alcohols, such as butyl alcohol, carboxylic acids such as butyric and hexanoic acid and bile salts such as sodium taurocholate and sodium glycocholate.

According to a preferred embodiment form of the present invention, in the preparation of the microemulsion the various substances are used in the following proportions, expressed as percentages by weight with respect to the total weight of the microemulsion:

| | |
|---|---|
| lipidic substance: | 5–18% |
| surfactants: | 10–20% |
| cosurfactants: | 12–18% |
| water: | 44–70% |

In the preferred embodiment form the lipidic nanospheres obtained by diafiltration have a titre in lipidic substance ranging from 25 to 42%, the residue consisting of phosphatidylcholine and/or phospholipids and by traces of other substances used in the preparation process.

According to a particularly preferred embodiment form of the present invention the composition of the solid lipidic nanospheres, expressed as percentage by weight of the various components, is the following one:

| | |
|---|---|
| cholesteryl butyrate | 31.5% |
| phosphatidylcholine | 68.0% |
| other | 0.5% |

Owing to their small size and their composition, said nanospheres have the unexpected characteristic to be rapidly internalised into cells, where the active substance is fast released.

With respect to the systems of the prior art, said solid lipidic nanospheres therefore are the ideal release system for active substances such as the low molecular weight carboxylic acids present in the esters of the present invention. In fact they allow a strong reduction of the effective doses, with subsequent limitation of the side effects.

The pharmaceutical compositions in form of solid lipidic nanospheres of the present invention may therefore be successfully used in the treatment of all the pathologies for which the above mentioned characteristics of fast internalisation of the active substance into the cells are important.

The pharmaceutical compositions in form of lipidic nanospheres object of the present invention are useful in the treatment of all the pathologies for which the administration of acetic acid, propionic acid, butyric acid and succinic acid is effective, and in particular in the treatment of the tumoral pathologies and of Mediterranean anaemia.

For said uses the nanospheres according to the invention may be used alone, or in a mixture with pharmacologically acceptable excipients and/or diluents, and/or pharmacologically active substances. In particular embodiment forms of the pharmaceutical compositions according to the present invention, said active substances are antineoplastic agents.

The following examples of preparation of pharmaceutical compositions in form of solid lipidic nanospheres are reported for illustrative, but not limitative purpose of the present invention.

EXAMPLE 1 a) 15 mg of Epikuron 200® (95% phosphatidylcholine) and 1 mg of phosphatidylinositol are added to 9 mg of cholesteryl butyrate, and such a mixture is heated to melting at about 75° C.;

b) a mixture consisting of water (62 mg), sodium glycocholate (3 mg) and butyl alcohol (10 mg) is heated at the same temperature of the mixture of the step a);

c) under mild stirring and at the same. temperature of the preceding steps, the mixture of the step b) is added to the mixture of the step a), obtaining a microemulsion, which turns out to be clear;

d) the microemulsion obtained in the step c) is dispersed in water precooled at 5° C. in an amount equal to 20 parts by volume of water for each part of microemulsion, obtaining a dispersion of nanospheres;

e) the dispersion obtained in the step d) is washed for 2 times with distilled water by diafiltration;

f) the washed dispersion is finally freeze-dried.

By photocorrelation spectroscopy the average diameter of the nanospheres has been determined, which turned out to be equal to 120 nm, with a polydispersion index equal to 0.25.

The so obtained nanospheres consist for 35.5% of cholesteryl butyrate and for 64% of phosphatidylcholine.

EXAMPLE 2 a) 16 mg of Epikuron 200® (95% phosphatidylcholine) are added to 7 mg of cholesteryl butyrate and heated to the melting of the mixture at about 77° C.;

b) at the same temperature of the step a) a mixture consisting of water (62 mg), sodium taurocholate (3 mg) and butyl alcohol (12 mg) is heated;.

c) the mixture of the step b) is added, under mild stirring and always at the same temperature of the previous steps, to the mixture of the step a), obtaining a clear microemulsion;

d) the microemulsion obtained in the step c) is dispersed in water precooled at 2° C. in an amount equal to 40 parts by volume of water for each part of microemulsion, obtaining a dispersion of nanospheres;

e) the dispersion obtained in the step d) is washed for 3 times with distilled water by diafiltration;

f) the washed dispersion is finally sterilised according to FU IX at 121° C. and at the pressure of 2 atmospheres.

The average diameter of the nanoparticles, determined by photocorrelation spectrometry, turned out to be 150 nm, with a polydispersion index equal to 0.35.

The so obtained nanospheres consist of 30% cholesteryl butyrate, and of 69% phosphatidylcholine.

Tests of Inhibition of the Cell Proliferation

The experimentation has been carried out on NIH-H460 cells of lung carcinoma (D. N. Carney et al., Cancer Res., 45, 2913–2923, 1985) grown in monolayer in the RPMI 1640 nutrient medium (Bio Whittaker, Verviers, Belgium) added with 10% by volume with respect to the total volume of FCS (Fetal Calf Serum), at the temperature of 37° C., in a $CO_2$ atmosphere humidified at 5%.

The cells have been put in 24 wells plates, using as nutrient medium RPMI 1640 added with 10% of FCS, and left to adhere for 24 hours. The insemination medium has been then removed and substituted with the experimental medium consisting of RPMI 1640 with 10% of FCS and increasing concentrations of sodium butyrate, or of cholesteryl butyrate in form of nanospheres prepared as in the above reported example 1. The cells have been kept for 6 days in contact with such experimental medium.

The effect of the sodium butyrate and of cholesteryl butyrate on the cell growth has been estimated counting the cells by a Cell Counter.

Thus it has been observed that the nanospheres containing cholesteryl butyrate induced a complete inhibition of the cell growth at a concentration equal to 0.21 mM of cholesteryl butyrate, while the sodium butyrate, at the same concentration, induced an inhibition of the cell growth limited to 50%.

Contemporaneously a comparison test has been carried out using cholesterol as an additive of the experimental medium consisting of RPMI 1640 with 10% FCS, by which it has been observed that the cholesterol does not affect the cell proliferation in any way.

The above described experiment has been repeated on cells of the mastocarcinoma, identified with the MCF7 abbreviation, using as insemination medium DMEM/F12 (Dulbecco's modified Eagle's medium, Sigma Chemical Co., St. Louis, Mo.) with 2% FCS.

Said cells have been placed in 12 well plates, where they have been left to adhere for 24 hours in the above described nutrition medium.

The nutrient medium has been then removed and substituted with the experimental medium consisting of DMEM/F12 with 10% FCS added with increasing concentrations of sodium butyrate, or of cholesteryl butyrate in form of nanospheres prepared according to the above reported example 2. The cells have been kept for 6 days in contact with such experimental medium.

The antiproliferative effect of the cholesteryl butyrate nanospheres on the cell growth has been estimated counting the cells with a Cell Counter. From such measurements turned out that the nanospheres containing cholesteryl butyrate induced a complete inhibition of the cell growth at a concentration equal to 0.2 mM of cholesteryl butyrate, while the sodium butyrate induced, at the same concentration, an inhibition of cell growth limited to 40%.

Tests on the Internalization in the Cells

The internalisation of the nanospheres containing cholesteryl butyrate in cells of the lung carcinoma, identified with the NIH-H460 abbreviation, has been studied by observation at the fluorescence microscope.

Operating according to the above reported example 1 nanospheres containing cholesteryl butyrate have been prepared, which have been made fluorescent by addition of cumarin 6.

NIH-H460 cells, added with 50 $\mu$l of tagged nanospheres, have been incubated at 37° C., and samples have been taken in different times to be examined.

Said samples have been washed with a saline solution buffered with phosphate buffer, centrifuged and added with a solution containing 5 $\mu$g/ml of propidium iodide.

The so treated cells have been observed and photographed by fluorescence microscope in parallel with the control consisting of the same cells added with propidium iodide only.

It has been observed that, contrary to the control, the cells treated with the nanospheres made fluorescent by cumarin 6 containing cholesteryl butyrate appeared almost totally fluorescent already after 5 minutes from the treatment, demonstrating an almost complete internalisation of the nanospheres in the cells in very short times.

What is claimed is:

1. A pharmaceutical composition useful in the treatment of tumoral pathologies and Mediterranean anaemia in the form of solid lipidic nanospheres having an average diameter lower than 300 nm and a polydispersion index ranging from 0.10 to 0.50, wherein said nanospheres consist essentially of cholesteryl butyrate, the amount of cholesteryl butyrate in the nanospheres is in the range from 25 to 42%, by weight, and a surfactant selected from the group consisting of phosphatidylcholine, phospholipids, and mixtures thereof.

2. The pharmaceutical composition as claimed in claim 1, wherein the content of cholesteryl butyrate is 31.5% by weight and the content of phosphatidylcholine is 68.0% by weight.

3. A process for the preparation of solid lipidic nanospheres as claimed in claim 1, comprising the following steps:
   a) heating a mixture comprising a lipidic substance and one or more surfactants at a temperature to take the mixture to the melting;
   b) heating a mixture consisting of water and one or more co-surfactants at a temperature equal to the temperature in step a);
   c) mixing under mild stirring the mixture of step b) with the mixture of step a), to form a microemulsion;
   d) dispersing the microemulsion obtained in step c) in precooled water;
   e) washing the dispersion of step d) with distilled water by diafiltration;
   f) freeze-drying or sterilizing the product obtained in step e), wherein said lipidic substance consists of cholesteryl butyrate and said surfactant is selected from the group consisting of soy phosphatidylcholine, egg phosphatidylcholine, phospholipids and their mixtures.

4. The process as claimed in claim 3, wherein the amount of said lipidic substance in said microemulsion of step c) is in the range from 5 to 18 %, by weight, with respect to total weight.

5. The process as claimed in claim 3, wherein the amount of water in the microemulsion of step c) is in the range from 44 to 70%, by weight, with respect to the total weight.

6. The process as claimed in claim 3, wherein the amount of surfactants present in the microemulsion of step c) is in the range from 10 to 20%, by weight, with respect to the total weight of the microemulsion.

7. The process as claimed in claim 3, wherein the amount of co-surfactants present in the microemulsion of step c) is in the range from 12 to 18%, by weight, with respect to the total weight of the microemulsion.

8. The process as claimed in claim 3, wherein said dispersion of step d) is carried out with water cooled to 2 to 10° C. in an amount in the range from 10:1 to 80:1 parts by volume with respect to the volume of the mixture of claimed step c).

9. A therapeutic method for the treatment of the tumoral pathologies and Mediterranean anaemia comprising the administration of an effective amount of the pharmaceutical composition claimed in claim 1.

* * * * *